US008170686B2

(12) United States Patent
Moreci et al.

(10) Patent No.: US 8,170,686 B2
(45) Date of Patent: May 1, 2012

(54) HEATABLE SLING SUPPORT FOR AN ANATOMICAL LOCATION

(75) Inventors: Stephen F. Moreci, Hopedale, MA (US);
Francis P. Grillo, Wellesley, MA (US);
Alfred P. Intoccia, Jr., Amherst, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1182 days.

(21) Appl. No.: 11/376,482

(22) Filed: Mar. 14, 2006

(65) Prior Publication Data

US 2007/0219606 A1 Sep. 20, 2007

(51) Int. Cl.
*A61F 7/00* (2006.01)
*A61F 2/02* (2006.01)
*A61F 2/04* (2006.01)

(52) U.S. Cl. ............ 607/101; 607/138; 600/29; 600/30; 600/37

(58) Field of Classification Search ............... 600/29, 600/30, 37; 607/101, 138
See application file for complete search history.

(56) References Cited

U.S. PATENT DOCUMENTS

| | | | | |
|---|---|---|---|---|
| 3,705,575 | A * | 12/1972 | Edwards | ............... 600/29 |
| 5,733,337 | A | 3/1998 | Carr, Jr. et al. | |
| 6,042,534 | A | 3/2000 | Gellman et al. | |
| 6,042,592 | A | 3/2000 | Schmitt | |
| 6,091,995 | A * | 7/2000 | Ingle et al. | ............... 607/138 |
| 6,127,597 | A | 10/2000 | Beyar et al. | |
| 6,216,704 | B1 * | 4/2001 | Ingle et al. | ............... 128/898 |
| 6,354,991 | B1 | 3/2002 | Gross et al. | |
| 6,375,662 | B1 | 4/2002 | Schmitt | |
| 6,418,930 | B1 * | 7/2002 | Fowler | ............... 128/830 |
| 6,463,331 | B1 | 10/2002 | Edwards | |
| 6,470,219 | B1 | 10/2002 | Edwards et al. | |
| 6,652,449 | B1 | 11/2003 | Gross et al. | |
| 6,666,817 | B2 | 12/2003 | Li | |
| 6,669,706 | B2 | 12/2003 | Schmitt et al. | |
| 6,752,814 | B2 | 6/2004 | Gellman et al. | |
| 6,755,781 | B2 | 6/2004 | Gellman | |
| 6,840,954 | B2 | 1/2005 | Dietz et al. | |
| 6,991,597 | B2 * | 1/2006 | Gellman et al. | ............... 600/37 |
| 7,070,558 | B2 | 7/2006 | Gellman | |
| 2001/0003798 | A1 | 6/2001 | McGovern et al. | |
| 2001/0020162 | A1 | 9/2001 | Mosel et al. | |
| 2002/0049425 | A1 | 4/2002 | Mosel et al. | |
| 2002/0062060 | A1 | 5/2002 | Gross et al. | |
| 2003/0009201 | A1 * | 1/2003 | Forsell | ............... 607/41 |
| 2003/0028180 | A1 | 2/2003 | Franco | |

(Continued)

FOREIGN PATENT DOCUMENTS

WO WO-98/19613 5/1998

(Continued)

OTHER PUBLICATIONS

Korni et al., "Outcome of Trans-Vaginal Radio Frequency for Treatment of Women with Stress Urinary Incontinence," University of Rochester Medical Center, p. 343.

(Continued)

*Primary Examiner* — Roy Gibson
*Assistant Examiner* — Kaitlyn Smith
(74) *Attorney, Agent, or Firm* — Bingham McCutchen LLP

(57) ABSTRACT

The invention provides, in various embodiments, systems, devices and methods relating to employing thermal treatment of tissue in combination with an implantable sling to treat urinary incontinence.

27 Claims, 9 Drawing Sheets

U.S. PATENT DOCUMENTS

| | | | |
|---|---|---|---|
| 2003/0144575 A1* | 7/2003 | Forsell | 600/29 |
| 2004/0073234 A1 | 4/2004 | Chu | |
| 2004/0116944 A1 | 6/2004 | Chu | |
| 2005/0038451 A1 | 2/2005 | Rao | |
| 2005/0038452 A1 | 2/2005 | Chu | |
| 2005/0096499 A1 | 5/2005 | Li | |
| 2007/0123746 A1* | 5/2007 | MacLean | 600/30 |
| 2007/0185541 A1* | 8/2007 | DiUbaldi et al. | 607/41 |
| 2007/0260288 A1* | 11/2007 | Gross | 607/41 |
| 2008/0009914 A1* | 1/2008 | Buysman et al. | 607/41 |
| 2009/0043356 A1* | 2/2009 | Longhini et al. | 607/41 |
| 2009/0259092 A1* | 10/2009 | Ogdahl et al. | 600/30 |
| 2010/0049289 A1* | 2/2010 | Lund et al. | 607/126 |
| 2010/0217340 A1* | 8/2010 | Watschke et al. | 607/2 |

FOREIGN PATENT DOCUMENTS

| | | |
|---|---|---|
| WO | WO 03/105727 | 12/2003 |
| WO | WO-2004/112656 | 12/2004 |

OTHER PUBLICATIONS

Surgery Section—Transanal Radiofrequency Treatment of Fecal Incontinence, The Regence Group, 3 pages, (2003).

Deurloo et al., "Application of a capacitive-coupling interstitial hyperthermia system at 27 MHz: study of difference applicator configurations," Phy Med. Biol, 36(1):119-132, (1991).

* cited by examiner

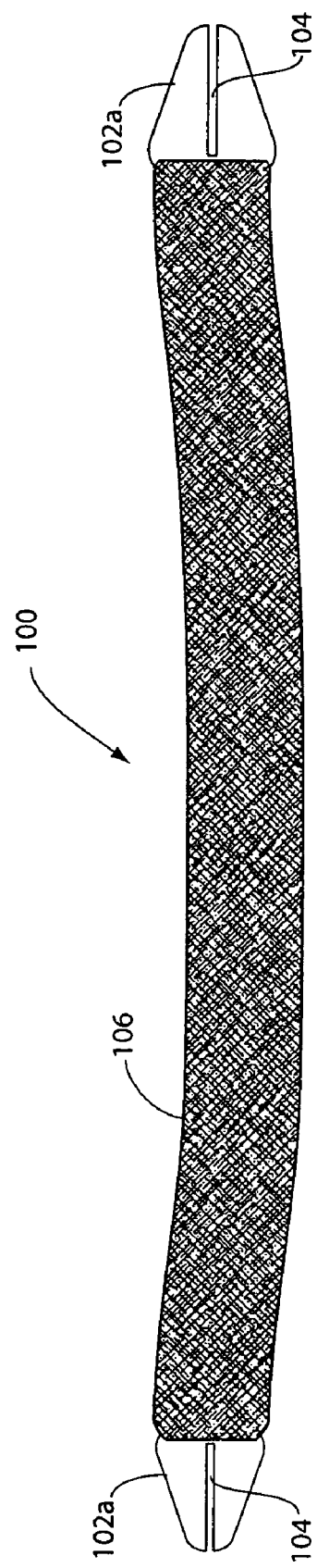

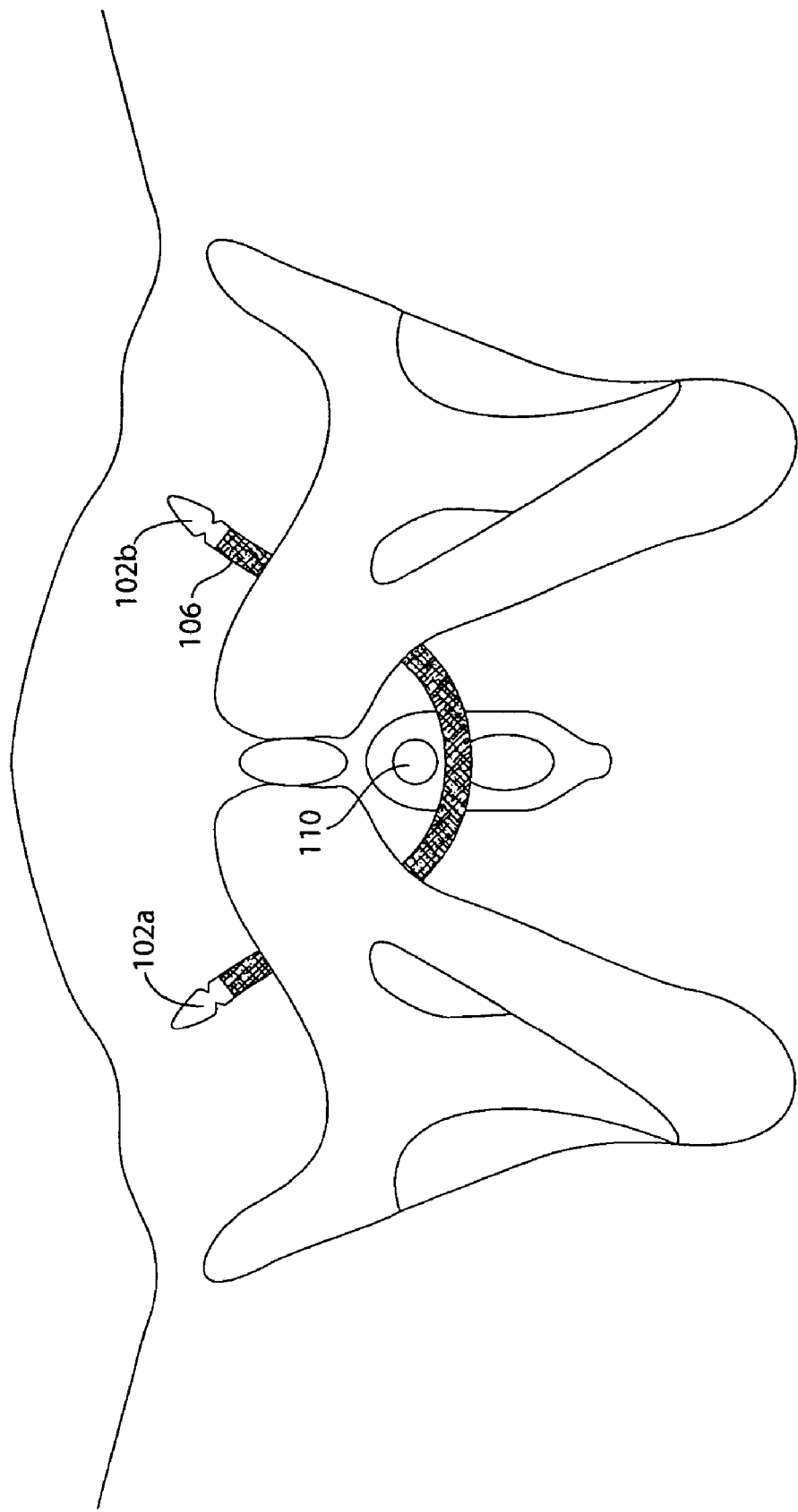

HEATABLE SLING SUPPORT FOR AN ANATOMICAL LOCATION

FIELD OF THE INVENTION

The invention generally relates to medical devices, methods, and systems for the treatment of urinary incontinence by applying a supportive sling to an anatomical location in a patient. More particularly, in various embodiments, the invention relates to a supportive sling that combines a mechanical sling support with an thermally induced contraction of surrounding tissues.

BACKGROUND OF THE INVENTION

Stress urinary incontinence (SUI) affects primarily women, but also men, and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvis floor is distended, weakened or damaged, causing the bladder neck and proximal urethra to rotate and descend in response to increases in intra-abdominal pressure (e.g., due to sneezing, coughing, straining, etc.). As a result, the patient's response time becomes insufficient to promote urethral closure and, consequently, the patient suffers from urine leakage and/or flow.

A popular treatment of SUI uses a surgical sling placed under the bladder neck or the mid-urethra to provide a urethral platform. Placement of the sling limits the endopelvis fascia drop. The sling can be affixed using a bone anchoring method or by an anchorless approach.

Another proposed treatment uses energy delivered to the patients' own pelvic support to selectively contract or shrink at least a portion of the pelvic support tissue, thereby raising the position of the bladder. However, the reported outcome for treatment of urinary incontinence with RF energy alone has indicated statistically disappointing or inconclusive success rates.

Accordingly, there is still a need for an improved approach for supporting the urethra to treat SUI and/or for providing support to other fascia, tendons, and other support tissues which have been strained, or which are otherwise too long to provide the desired support.

SUMMARY OF THE INVENTION

The systems and methods described herein are generally directed to the treatment of stress urinary incontinence. More particularly, in various embodiments, the invention provides systems and methods relating to delivering a supportive sling to the periurethral tissue of a patient, wherein the sling is constructed to promote shrinkage of the collagenated tissues proximate to the supportive sling. The present invention relies on delivering energy to the supportive sling to raise the temperature around the pelvic support tissue. At least a section of the supportive sling is electrically conducting, so that this section can be selectively heated. A variety of devices and methods are provided for applying gentle radio-frequency (RF) heating to the conducting sling or sling sections, without significant injury to the support tissues or the surrounding tissue structures.

According to one aspect, a sling assembly for supporting an anatomical location in a patient includes an implantable sling sized and shaped for providing support to tissue at the anatomical location, and an electrically conductive element disposed in or on the implantable sling and couplable to an electromagnetic excitation source.

According to another aspect, a system for applying thermal energy to an anatomical location in a patient includes an implantable sling sized and shaped for providing support to tissue at the anatomical location, an electrically conductive element disposed in or on the sling, and an electromagnetic excitation source coupling energy to the electrically conductive element for conversion into thermal energy.

According to yet another aspect, a method for supporting an anatomical location in a patient includes implanting a sling sized and shaped for providing support to tissue at the anatomical location, coupling an electromagnetic excitation source to an electrically conductive element disposed in or on the sling to produce thermal energy, and heating the tissue proximate to the anatomical location by applying to the tissue the thermal energy produced by the electrically conductive element.

According to yet another aspect, the supportive sling having an electrically conductive element disposed in or on the sling can be used for treatment of urinary incontinence by implanting the sling at an anatomical location of a patient, and coupling an electromagnetic excitation source to the electrically conductive element to produce thermal energy. This heats the tissue proximate to the anatomical location and strengthens or tightens the tissue to provide added support for the urethra.

Shrinking the collagenated tissues around an implanted sling support can also facilitate removal of the sling support from the patient's body after the collagenated tissues has become strong enough to support the pelvic support tissue. According to another aspect, the sling can be removed from an anatomical location in a patient by coupling an electromagnetic excitation source to an electrically conductive element disposed in or on the sling to produce thermal energy and thus heat the tissue proximate to the anatomical location, and externally applying a pulling force to the sling to pull the sling away from the anatomical location.

Embodiments of the invention may include one or more of the following features. The sling may include end terminations, with the electrically conductive element extending between the end terminations of the sling. The electrically conductive element may be applied uniformly along the length of the sling between the end terminations. Alternatively, the electrically conductive element may include low-resistance end portions located proximate to the end terminations, and one or more additional electrically conductive portions with a higher electrical resistance than the end portions, which can be electrically connected to the low-resistance sections. The additional sections may have a reduced thickness compared to the end portions and/or made of a different material than the end portions and/or may be made of a perforated conductive sheet. It will be understood that several of these features may be used in combination.

In this way, more thermal energy can be generated in selected areas. Contact portions may disposed on or near the end terminations for connection to an external source of electric energy, or to an internal, for example, implanted source of electric energy.

In one embodiment, the electrically conductive element may extend over only a portion of the sling, with the sling portion being located at a location of the sling intended for heating and supporting the tissue at the anatomical location. The electrically conductive element may include at least one electrically conductive strand, such as a wire or filament, which may be applied to and/or woven into the sling. The stand may be made of a metal wire, metal-coated plastic, metal-coated insulator, metal-dispersed insulator, semiconductor, and/or a conductive polymer. Alternatively or in addition, the electrically conductive element may include a dispersed electrically conducting material.

In some embodiments, the electrically conductive strands may be substantially non-overlapping, thereby forming individual conductors. In other embodiments, the electrically conductive strands may overlap at predetermined contact points so as to form electrically conducting loops.

Electric energy can be supplied to the electrically conductive portions or elements of the sling either resistively, or can be coupled capacitively or inductively, for example, by using an RF field. The RF field can be applied, for example, with a handheld probe having a probe tip with one or more electrodes or with an RF coil.

Further features and advantages of the invention will be apparent from the following description of illustrative embodiments and from the claims.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIG. 1A is a schematic diagram of a supportive sling with end terminations for treatment of urinary incontinence;

FIG. 1B is a conceptual diagram showing affixation of a sling end terminations to soft tissue;

DETAILED DESCRIPTION OF CERTAIN ILLUSTRATED EMBODIMENTS

Figure 1C:
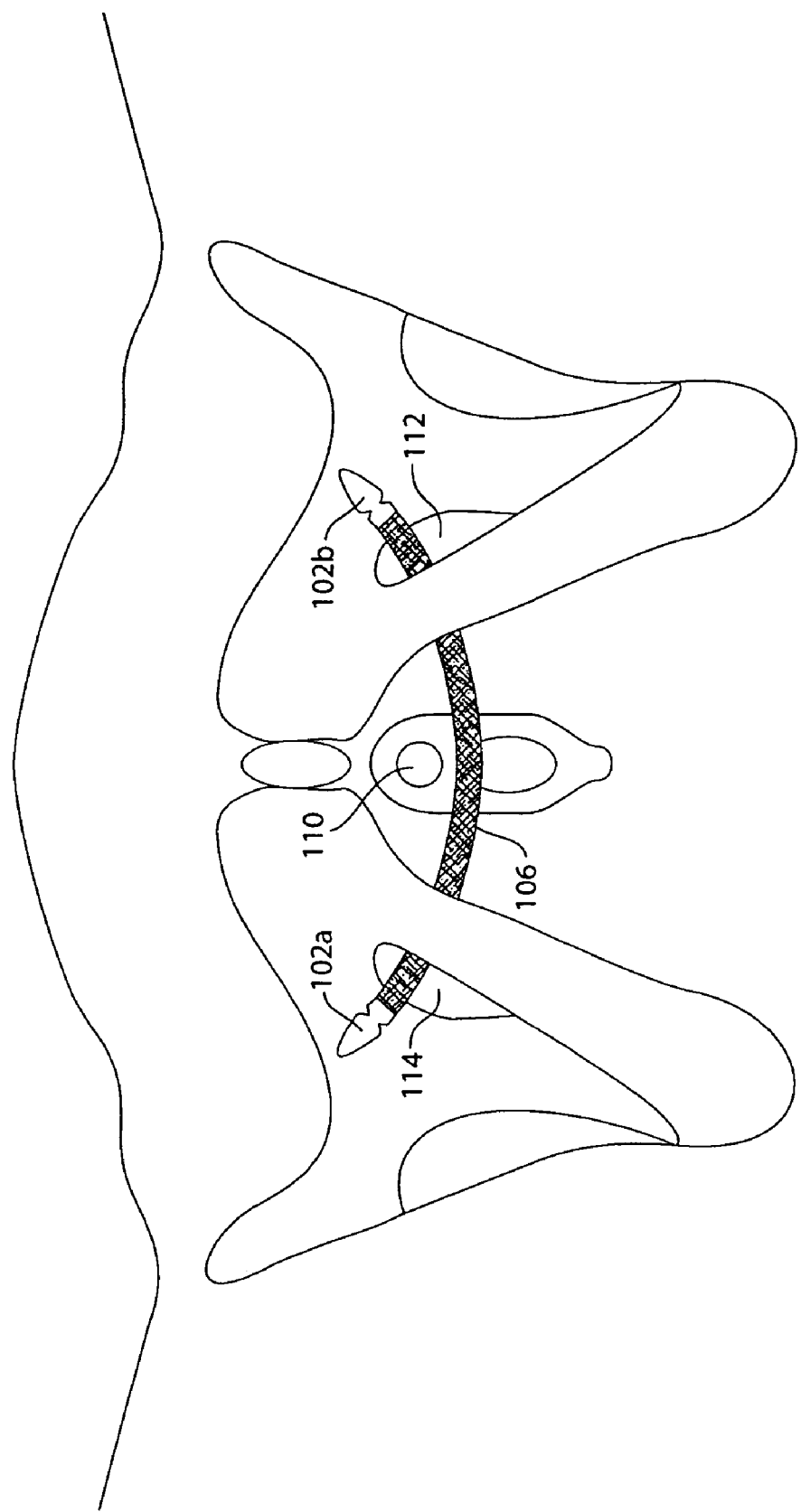
FIG. 1C is a conceptual diagram showing affixation of a sling end terminations to an obturator membrane.

In general, the invention is directed to systems, methods and devices for treating urinary incontinence. As described below in more detail, in various illustrative embodiments, the invention provides systems, methods and devices employing thermal treatment of the tissue surrounding an implanted supportive sling by directly producing thermal energy in the sling.

Without limitation, examples of slings, sling assemblies, sling delivery devices and approaches, sling assembly-to-delivery device association mechanisms, and sling anchoring configurations with which the invention may be employed are disclosed in U.S. Pat. No. 6,042,534, entitled "Stabilization Sling for Use in Minimally Invasive Pelvic Surgery," U.S. Pat. No. 6,755,781, entitled "Medical Slings," U.S. Pat. No. 6,666,817, entitled "Expandable Surgical Implants and Methods of Using Them," U.S. Pat. No. 6,042,592, entitled "Thin Soft Tissue Surgical Support Mesh," U.S. Pat. No. 6,375,662, entitled "Thin Soft Tissue Surgical Support Mesh," U.S. Pat. No. 6,669,706, entitled "Thin Soft Tissue Surgical Support Mesh," U.S. Pat. No. 6,752,814, entitled "Devices For Minimally Invasive Pelvic Surgery," U.S. patent application Ser. No. 10/918,123, entitled "Surgical Slings," U.S. patent application Ser. No. 10/641,376, entitled "Spacer for Sling Delivery System," U.S. patent application Ser. No. 10/641,192, entitled "Medical Slings," U.S. patent application Ser. No. 10/641,170, entitled "Medical Slings," U.S. patent application Ser. No. 10/640,838, entitled "Medical Implant," U.S. patent application Ser. No. 10/460,112, entitled "Medical Slings," U.S. patent application Ser. No. 10/631,364, entitled "Bioabsorbable Casing for Surgical Sling Assembly," U.S. patent application Ser. No. 10/092,872, entitled "Medical Slings," U.S. patent application Ser. No. 10/939,191, entitled "Devices for Minimally Invasive Pelvic Surgery," U.S. patent application Ser. No. 10/774,842, entitled "Devices for Minimally Invasive Pelvic Surgery," U.S. patent application Ser. No. 10/774,826, entitled "Devices for Minimally Invasive Pelvic Surgery," U.S. patent application Ser. No. 10/015,114, entitled "Devices for Minimally Invasive Pelvic Surgery," U.S. patent application Ser. No. 10/973,010, entitled "Systems and Methods for Sling Delivery and Placement," U.S. patent application Ser. No. 10/957,926, entitled "Systems and Methods for Delivering a Medical Implant to an Anatomical Location in a Patient," U.S. patent application Ser. No. 10/939,191, entitled "Devices for Minimally Invasive Pelvic Surgery," U.S. patent application Ser. No. 10/918,123, entitled "Surgical Slings," U.S. patent application Ser. No. 10/832,653, entitled "Systems and Methods for Sling Delivery and Placement," U.S. patent application Ser. No. 10/642,397, entitled "Systems, Methods and Devices Relating to Delivery of Medical Implants," U.S. patent application Ser. No. 10/642,395, entitled "Systems, Methods and Devices Relating to Delivery of Medical Implants," U.S. patent application Ser. No. 10/642,365, entitled "Systems, Methods and Devices Relating to Delivery of Medical Implants," U.S. patent application Ser. No. 10/641,487, entitled "Systems, Methods and Devices Relating to Delivery of Medical Implants," U.S. patent application Ser. No. 10/094,352, entitled "System for Implanting an Implant and Method Thereof," U.S. patent application Ser. No. 10/093,498, entitled "System for Implanting an Implant and Method Thereof," U.S. patent application Ser. No. 10/093,450, entitled "System for Implanting an Implant and Method Thereof," U.S. patent application Ser. No. 10/093,424, entitled "System for Implanting an Implant and Method Thereof," U.S. patent application Ser. No. 10/093,398, entitled "System for Implanting an Implant and Method Thereof," and U.S. patent application Ser. No. 10/093,371, entitled "System for Implanting an Implant and Method Thereof," the entire contents of all of which are incorporated herein by reference.

FIG. 1A shows an illustrative sling assembly 100 having a supportive sling 106 and employing end terminations 102a and 102b which can be configured to slidably associate the depicted sling 106 with a delivery device (not shown). The sling 106 may be wrapped around or inserted and clamped in a slot disposed in the exemplary end terminations 102a and 102b, which may be tapered to operate as tissue dilators. By way of example, and without limitation, the end termination 102a and/or 102b may or may not include barbs disposed on the outside surface of the end terminations, for example, for providing tissue anchoring, may be tubular in nature, and may or may not include an axially extending through aperture 104 for insertion of a delivery device (not shown). Any suitable end termination 102a and/or 102b of the sling 106 may be employed. The type of end termination is not critical to the scope of the invention. The sling assembly 100 may include any suitable features disclosed in any of the patents and patent applications incorporated herein by reference.

The sling 106 may have a length of about 10 to about 15 cm (about 4-6 inches) and a width of about 1 to about 3 cm, though the length and width of the sling 106 can be adapted to the body part of the patient that requires support. By way of example, in some embodiments, the sling 106 is about 45 cm in length. The sling 106 may be substantially rectangular, as illustrated in FIG. 1A, or have another suitable shape. The sling 106 may have a uniform thickness over the entire length and/or width of sling 106. Alternatively, the thickness can be suitably varied at one or more locations. The thickness of the sling material may range, for example, from about 0.02 to about 0.10 cm. In one illustrative embodiment, the sling 106 is formed from a strip of mesh with any of a plurality of configurations of knits, weaves, or braids.

The sling 106 may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials can include polyglycolic acid, polylactic acid, and other suitable absorbable synthetic materials. Alternatively, the material for the sling 106 may be derived from mammalian tissue(s) or a combination of mammalian tissue(s) and synthetic material(s). The sling material may be fabricated from one or more yarns, which yarns may be made from one or more materials. The sling 106 may incorporate or be coated with one or more agents to provide a therapeutic effect, for example, to reduce discomfort, to reduce the chance of infection and/or to promote tissue growth.

Depending on the specific design of the sling, the sling can be implanted via an initial transvaginal incision, or sometimes via additional abdominal or ishiopubic incisions. The particular method of implanting the sling is not the subject of the present invention. An exemplary method, such as the method using the aforedescribed end terminations or bone anchors 102a, 102b illustrated in FIGS. 1B and 1C, is merely provided to illustrate the general placement of the supportive sling 106 below the urethra.

FIG. 1B shows a sling 106 implanted in the periurethral tissue of a patient to form a platform under the urethra 110. The sling assembly 100 is implanted, for example, by making an incision (not shown) in the anterior vaginal wall. A medical operator interfits the end termination 102a, such as a soft tissue anchor, and a distal end of a delivery device shaft (not shown) and passes the device shaft with the end termination 102a installed through the vaginal incision and upward into a desired anchoring location on a first side of the urethra 110, preferably, without piercing the abdomen. The anchoring location may be in any suitable abdominal soft tissue, such as without limitation, the retropubic space between the bladder and the abdomen, the space of Retzius, or the Cooper's ligament. Additionally, the anchoring location may be in front of or behind the pubic bone. Once the end termination 102a is placed at the desired location, the delivery device shaft can be withdrawn leaving the end termination 102a in place. The procedure is repeated on the contralateral side of the body, with the same or a second delivery device operating on end termination 102b, for final placement of the sling 106 under the urethra, as shown in FIG. 1B. If two separate delivery devices are used and both delivery devices remain initially connected to the end terminations 102a, 102b, then these delivery devices can also be operative to deliver electric energy to the sling 106, as described below.

In another illustrative embodiment depicted in FIG. 1C, at least one of the first 102a and second 102b end terminations of the sling assembly 100 may be positioned near or through an obturator foramen (i.e., transobturally) and/or obturator membrane. In this embodiment, a medical operator inserts a delivery device shaft (not shown), with the end termination 102a installed, through a vaginal incision in a lateral motion passing behind the ishiopubic ramus and piercing the obturator membrane 112. The delivery device shaft can then be withdrawn from the body leaving the end termination 102a implanted in or through the obturator membrane 112. This process is repeated with the same or a second delivery device and the second soft tissue end termination 102b on the contralateral side of the body, piercing the obturator membrane 114. Again, these delivery devices can also be operative to deliver electric energy to the sling 106.

According to various illustrative embodiments, the supportive sling assembly 100 may be made of any suitable biocompatible material. The supportive sling assembly 100 may be made, for example, of a synthetic material such as nylon, polyethylene, polyester, polypropylene, fluoropolymers or a co-polymer thereof. In some illustrative embodiments, they may be formed, at least in part, from a mammalian tissue material such as bovine, porcine, equine, human cadaver or engineered tissue. In some illustrative embodiments, the material of the sling assembly 100 may include a combination of synthetic and mammalian tissue materials. According to another feature, at least a portion of the sling assembly 100 may be biodegradable and may also dissolve and/or be absorbed into the patient's tissues.

According to another feature, the sling assembly 100 may be configured to dissolve within a particular time range. The sling assembly 100 may be configured, for example, to substantially absorb (or have a portion that substantially absorbs) into the patient's tissues within about 2, 4, 6 or 8 or more weeks from the time the sling is implanted. Preferably, the sling assembly 100 remain structurally intact long enough for scar tissue and/or other neighboring cells or tissues to grow into the sling 106 to keep the sling in place.

According to other illustrative embodiments, the sling 106 may be treated with one or more agents for release into the patient's tissues. One illustrative agent promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the sling 106. This may be controlled by selecting differing methods for loading the agent onto the sling 106. The tissue growth factor may include natural and/or recombinant proteins for stimulating a tissue response so that collagenous tissue, such as scar tissue, growth is enhanced. The tissue growth factor may similarly include natural and/or recombinant proteins for stimulating a tissue response so that tissue growth is enhanced. Furthermore, the tissue growth factor may include non-protein, protein, small molecule agents that mimic the effects of a natural and/or recombinant protein on scar or non-scar tissue growth. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. Exemplary small molecule growth factors include, but are not limited to, small molecule agents that mimic the effects of one or more of the foregoing growth factors. The agent may also include a hormone, including but not limited to estrogen, steroid hormones, and other hormones to promote growth of appropriate collagenous tissue such as scar tissue. The agent may also include stem cells or other suitable cells derived from the host patient or derived from a suitable donor. Suitable cells include, without limitation, embryonic stem cells, adult stem cells, and other suitable non-stem cells. Stem or non-stem cells may be fibroblastic, mesenchymal, myoblastic, endothelial, and other cell types capable of maturing into appropriate tissues.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof. Such therapeutic agents include protein and non-protein, small molecule agents.

According to another illustrative embodiment, the sling 106 may be treated with one or more inflammatory agents for release into the patient's tissues. Inflammatory agents may include, for example, oleoresin capsicum, orthochlorobenzalonoitrate, prostaglandins, antiprogesterone, relaxin, histamines, glucocorticoids, leukotrienes, thromboxanes, C5a, TNF-alpha, NF-Kappa-B, GM-CSF, interleukins, IL-18, IL-8, IL-6, IL-1β, IL-1 alpha, iNOS, TGFβ, Resistin, pro-inflammatory cytokines, agonists or promoters of pro-inflammatory cytokines, bacterial lipopolysaccharide (LPS), phorbol ester, TPA, NO, superoxide, macrophage colony-stimulating factor, cyclophilins, chemokines, eicosanoids, COX-1, COX-2, PLA2, bi- and tri-specific antibodies. When applied to the patient's tissues in a pharmaceutically acceptable amount, inflammatory agents stimulate the rate of tissue in-growth to ensure that the sling is anchored rapidly in the surrounding tissue, while maintaining the sling tension applied at the time of surgical placement of the sling. The inflammatory response can thus enhance the thermal effects produced by heating the tissue.

The RF energy can be applied to the tissue with probes which are moved by the practitioner across the area to be treated. Bipolar electric current is resistively coupled into the tissue through an electrode either in a single electrode configuration (where a ground plate is attached to the patient) or a dual electrode configuration (where the current flows between two electrodes). The temperature of the target tissue structure can be raised to a value in the range from 70° C. to 95° C., for a time sufficient to effect the desired tissue shrinkage, for example, from 1 minute to 2 minutes. The total amount of energy delivered will depend in part on which tissue structure is being treated as well as the specific temperature and time selected for the protocol. The power delivered will often be in the range from 2 W to 5 W. However, according to several medical reports, the benefits obtained by treating urinary incontinence, and also fecal incontinence, with RF energy alone were found to be statistically inconclusive.

Moreover, delivery of RF energy to tissue is difficult due to the low RF conductivity of tissue. Direct tissue heating by RF is a function of many parameters, including the mass, thermal conductivity, and heat capacity of the body part under study; its level of blood perfusion; ambient temperature; air circulation; the specific pulse sequence; and RF frequency. The FDA has used the tissue RF specific absorption rate (SAR) as the parameter of heating to establish guidelines for allowable RF energy deposition. The SAR is expressed in units of watts per kilogram of body weight (W/kg). The general guideline used by the FDA to establish allowable RF energy deposition is based on levels that produce a maximum change in tissue temperature of 1° C. According to the specific FDA criteria for SAR limits, the SAR must be no greater than (a) 4 W/kg averaged over whole body for any 15-minute period, (b) 3 W/kg averaged over the head for any 10-minute period, or (c) 8 W/kg in any gram of tissue in the head or torso or 12 W/kg in any gram of tissue in the extremities for any period of 5 minutes.

As mentioned above, attempts have been made to treat urinary incontinence without a supportive sling by transvaginally applying a RF signal directly to the endopelvic fascia to selectively shrink fascia and other collagenated tissue. Tissue contraction results from controlled heating of the tissue by affecting the collagen molecules of the tissue. Contraction may occur as a result of heat-induced uncoiling as the collagen β-pleated structure and subsequent re-entwinement as the collagen returns to body temperature.

According to the illustrative embodiment, electric energy, such as RF energy, may be applied to an electrically conducting material or structure disposed on or in the sling 106. The RF energy then can be selectively coupled to the conducting material to controllable heat the conducting material, to transfer thermal energy to the tissue near and/or surrounding the conducting material or structure.

Figure 2A:
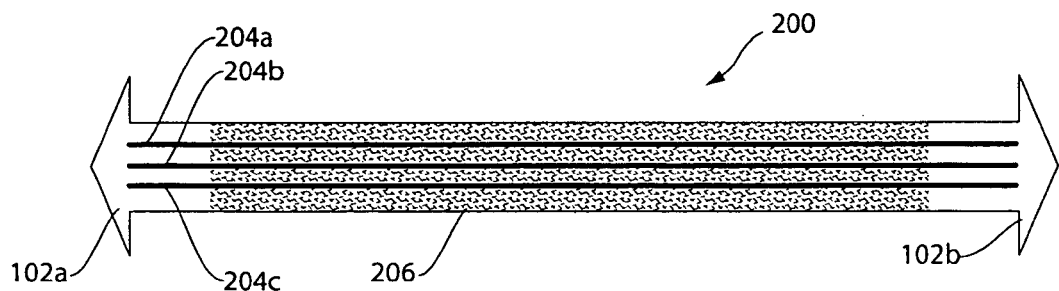
FIG. 2A is a conceptual diagram of a sling according to an illustrative embodiment of the invention with electrically conductive elements.
Figure 5:
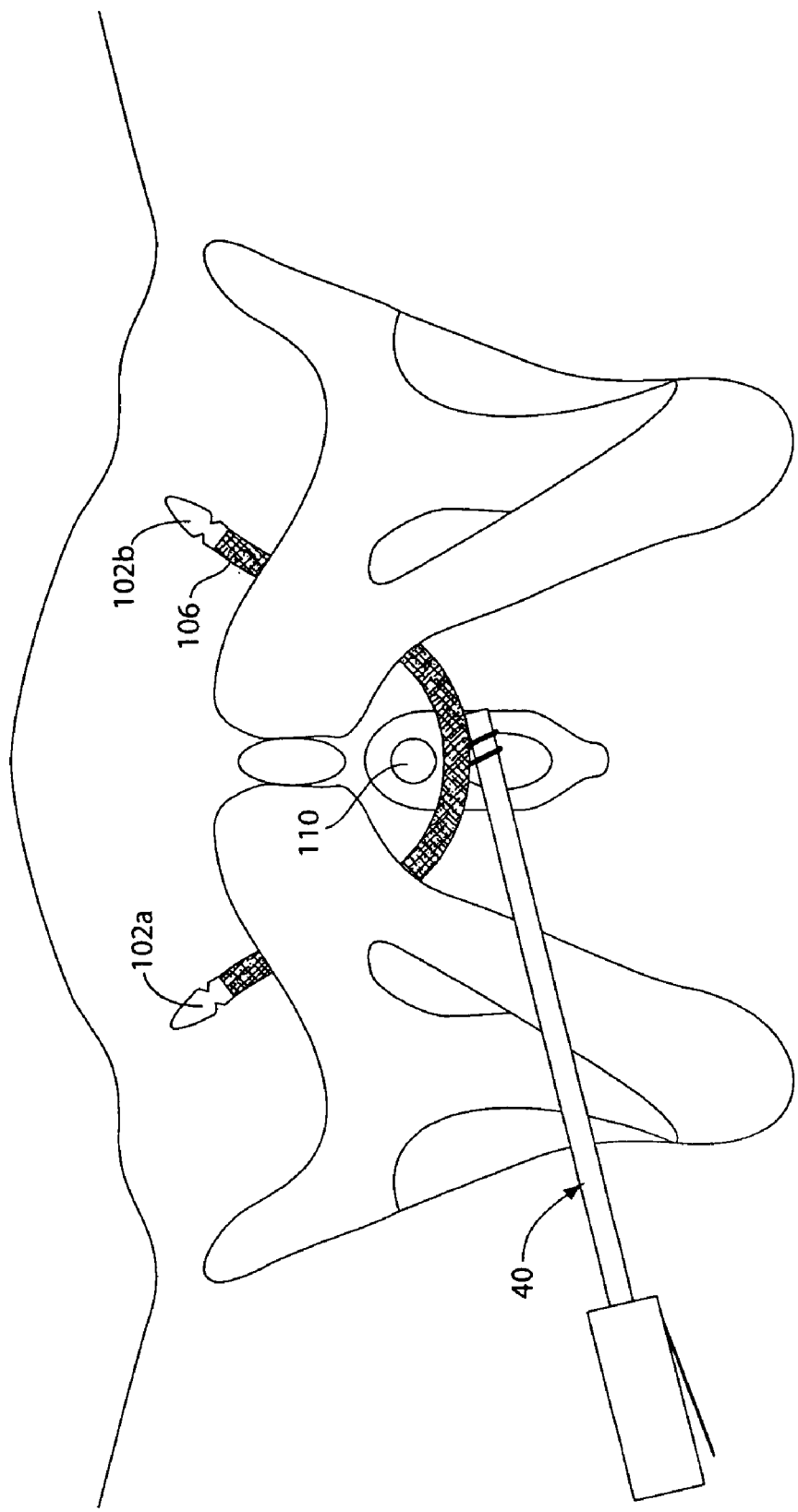
FIG. 5 shows schematically application of RF energy to a section of an electrically conductive sling using the RF probe of FIG. 4A.

FIG. 2A shows a sling assembly 200 including electrically conducting, preferably biocompatible, conductors 204a, 204b, 204c applied to or woven into the fabric of an implantable supportive sling 206. The conductors can be straight and extend continuously from one of the end terminations 102a to the other end termination 102b of the sling 206. An RF current can be resistively or capacitively coupled to the conductors 204a, 204b, 204c between the end terminations 102a and 102b, for example, by connecting a delivery device described in further detail below to a current source and/or a RF source, to heat the conductors 204a, 204b, 204c and thus the sling 206 and the tissue surrounding the sling 206. An exemplary arrangement for coupling a current and/or RF source (which can be internal or external to the patient's body) is shown schematically in FIG. 5.

Figure 2B:
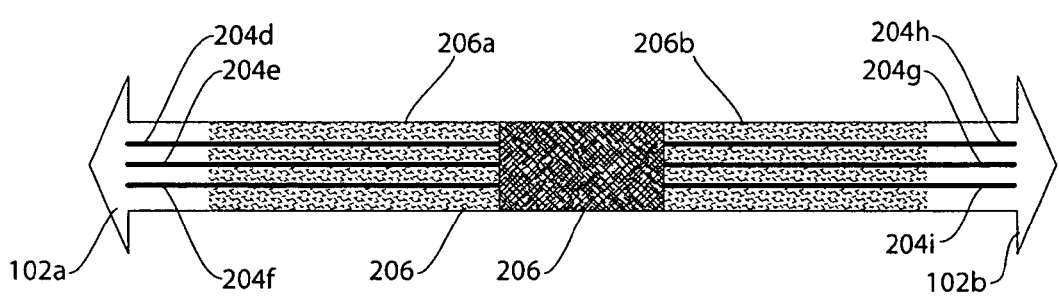
FIG. 2B is a conceptual diagram of a sling according to an illustrative embodiment of the invention with electrically conductive elements forming a heated zone.

As illustrated in FIG. 2B, an exemplary heating zone 208 may be formed at a predetermined location or in a predetermined area of the sling 206, for example, by providing electrical conductors with a low electrical resistance R in the end sections 206a and 206b of sling 206, while the configuring the heating zone 208 to have a relatively high electrical resistance R. Since the dissipated power P is $P=R*i^2$ (i=electric current), more heat is generated in the heating zone 208 with the higher resistance, so that the tissue surrounding the heating zone 208 is heated to a higher temperature than the rest of the sling 206. Such high-resistance heating zones 208 can be produced, for example, by providing a pattern of apertures in an otherwise continuous electrical conductor section located proximate to the urethra 110. The higher current density in the conductive material surrounding the holes will cause a substantial temperature increase compared to the low resistance end sections, channeling the generated heat into the sling area supporting the urethra 110 and heating the surrounding tissue. The electrical resistance may be increased in other ways, for example, by making the conductive heating zone 208 of a different material with a higher resistance, or by decreasing the thickness of the resistive material. Although only one illustrative heating zone 208 is shown in FIG. 2B, more than one heating zone may be arranged on the sling 206, each of which may be directly connected to the end sections 206a and 206b. Such heating zones may be connected in parallel or in series, with the respective ends of the series connection connected to the end sections 206a and 206b.

Figure 2C:
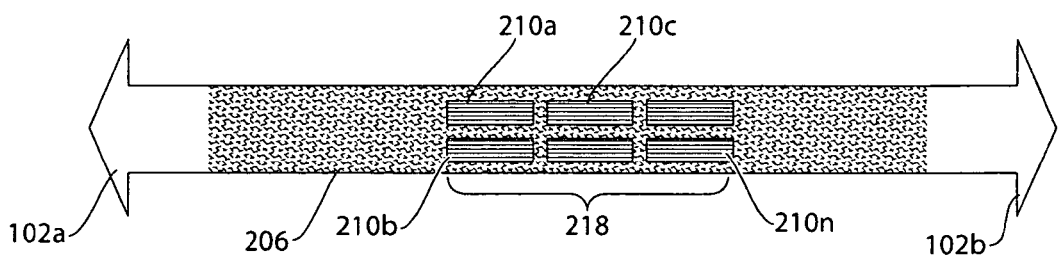
FIG. 2C is a conceptual diagram of a sling according to an illustrative embodiment of the invention with electrically conductive elements suitable for coupling RF energy.

According to another illustrative embodiment depicted in FIG. 2C, one or more electrical conductors 210a, 210, 210c, 210d, . . . , and 210n may be applied to or woven into the supportive sling 206 over only a section 218 of the sling 206, such as a center portion supporting the urethra 110. The exemplary electrical conductors 210a, . . . , 210n may be elongated, as shown in FIG. 2C, and may be energized resistively or capacitively by connecting a probe, such as the probe of FIG. 4A, to an RF source. As described in further detail below with respect to FIG. 4A, the electric RF field generated between two electrodes 48 and 50 of the probe 40 couples to the electrical conductors 210a, . . . , 210n in the sling section 218. Capacitive coupling does not require galvanic contact between the probe electrodes 48 and 50 and the electrical conductors 210a, . . . , 210n.

Figure 2D:
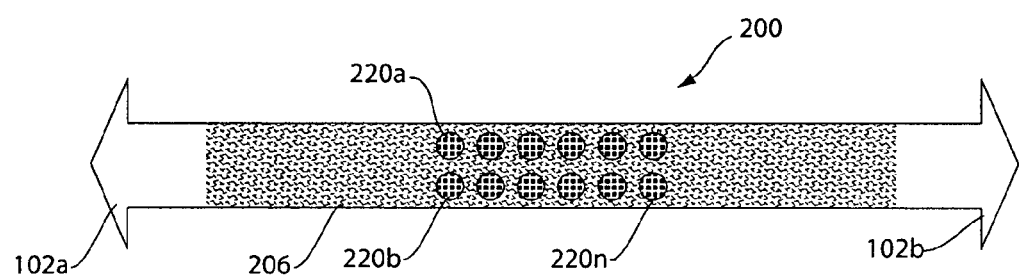
FIG. 2D is a conceptual diagram of a sling according to another illustrative embodiment of the invention with electrically conductive elements suitable for coupling RF energy.

In an alternative illustrative embodiment shown in FIG. 2D, electrical conductors 220a, 220n may have a round or polygonal shape. According to this embodiment, a single-ended RF electrode may be used, with a counter-electrode implemented as a grounding plate in contact over a relatively large area of the patient's body. The RF current then flows from the single probe electrode, for example electrode 48 in FIG. 4A, through the conductive structure, such as the conductors 220a, . . . , 220n, and the patient's body to the ground plate.

According to one illustrative embodiment, the electrical conductors described above can be implemented as electrically conducting fibers, for example, fibers made of a conductive polymer, such as conductive polymer strands commercially available from Santa Fe Science and Technology, Santa Fe, N.Mex., USA and sold under the name Panion™. Other conductive polymers, such as tetrathiafulvalene-tetracyanoquinodimethane (TTF-TCNQ), may also be used. The conductive polymer can be woven into the existing sling geometry and should be biocompatible, but may also be biodegradable. More generally, the employed conductive polymer may have a biocompatibility similar to that of the sling material.

Figure 2E:
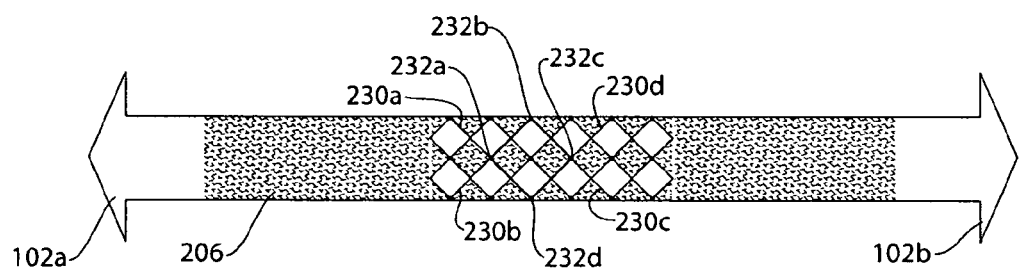
FIG. 2E is a conceptual diagram of a sling according to another illustrative embodiment of the invention with electrically conductive elements suitable for inductive coupling RF energy.

FIG. 2E shows another illustrative embodiment in which RF energy may be inductively coupled to the sling 206 or a portion of the sling 206. According to this illustrative embodiment, electrically conducting objects, such as wires, plates and dispersed conducting particles, are located in the sling 206. When placed near an alternating magnetic field, such as an RF field, they may be caused to heat up. Energy transfer in inductive coupling becomes more efficient when the metallic object is configured as a closed conductive loop or coil. According to the illustrative embodiment, conductive loops are formed by applying electrical conductors 230a, 230b, 230c, 230d, . . . , 230n into the fabric of sling 206 and selectively interconnecting the conductors at predetermined crossing points, such as the depicted exemplary crossing points 232a, 232b, 232c, 232d. One exemplary loop is formed by the conductors 230a, 230b, 230c, 230d, which are connected at the crossing points 232a, 232b, 232c, 232d. Coupling efficiency depends on the quality factor Q of the loop or coil arrangement, which is determined, at least in part, by the internal resistance and capacitance of the corresponding loop or coil. Other circuit elements, such as capacitors, may also be formed on the sling to tune the resonance frequency and Q factor of the arrangement. According to one illustrative example, the conductive loops are formed by weaving conductors through the sling fabric.

According to one advantage of the invention, inductive coupling does not require direct contact with the sling 206 or its components, so RF power can be transferred to the heated zone of sling 206 without disturbing the surrounding tissue. Moreover, RF energy can be inductively coupled to any conductive component or structure regardless of its shape or physical dimension, which may only affect the coupling efficiency.

Figure 3:
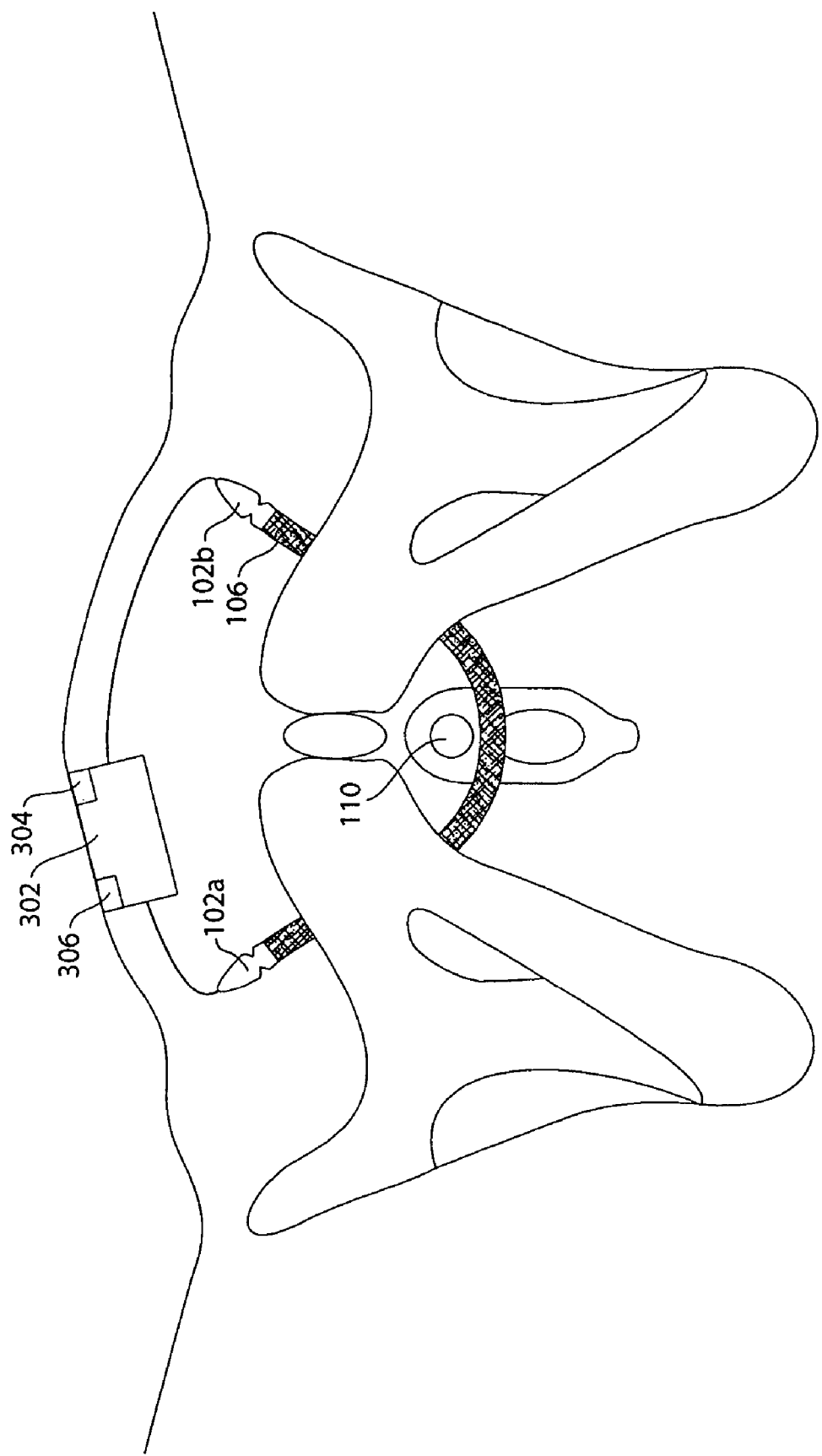
FIG. 3 is a conceptual diagram of an electrically conductive sling connected to an implanted energy source.

Turning now to FIG. 3, according to another illustrative embodiment, RF energy or resistive current for heating the sling 206 or portions of sling 206 may be applied, for example, by coupling an implantable energy coupler or energy source 302 to conductive portions of the sling 206, such as the end terminations 102a and 102b. The implantable energy source 302 may be placed, for example, subcutaneously in the abdomen and may include a battery 304 and/or an inductive coil 306, which may be used to remotely charge the battery 304 through the skin or apply energy directly to the end terminations 102a and 102b. Selective application of energy, even after implantation of the sling 206, can then be used, for example, to treat or tighten the tissue surrounding the sling 206 as needed. An exemplary implantable energy source 302 that may be used with the invention is Bion™ energy source, available from Advanced Bionic Corp., Valencia, Calif.

According to another illustrative embodiment, the sling 206, or at least a heated section of the sling 206, may include a therapeutic agent for lifting or otherwise modifying the muscle tissue supporting the bladder and/or urethra. The therapeutic agent may also include drugs that enhance the therapeutic effect of the sling 206.

According to a further illustrative embodiment, energy may be applied to the sling 206 for the purpose of dissolving or removing the sling material after implantation. This concept was tested by implanting conductive esophageal stents in pigs, where the stents remained for >7 days to allow tissue ingrowth. Esophageal stents are typically made either from Nitinol™ metal, which is a titanium-nickel alloy, or stainless steel. When RF power was subsequently applied to the stents, the stents could be removed by pulling with minimal applied force.

Figure 4A:
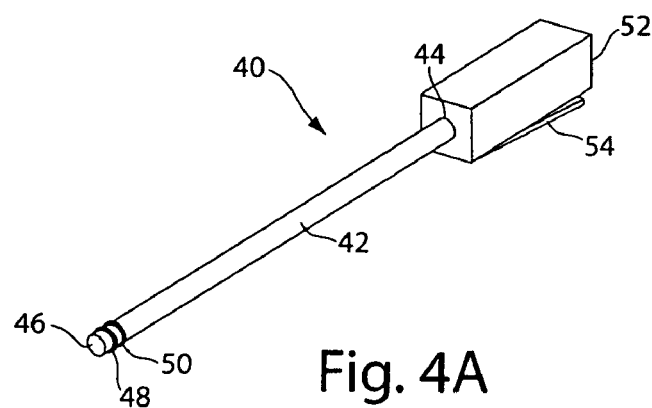
FIG. 4A-4B shows schematically a handheld RF probe for coupling RF energy into a conductive sling material and functional components of the RF probe.
Figure 4B:
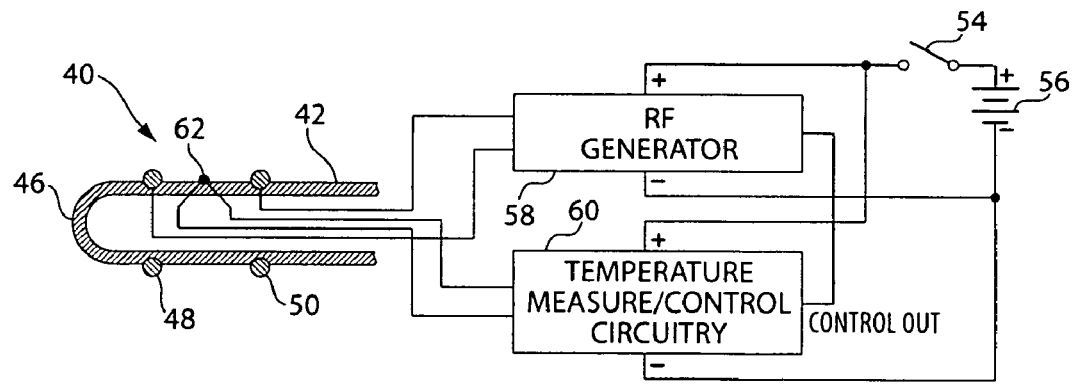

FIGS. 4A and 4B show schematically an exemplary handheld RF excitation probe 40 for coupling RF energy from an RF generator 58, which can be incorporated in a handle 52 of probe 40, into the conductive portion of sling 206, as described above. Exemplary probe 40 includes a shaft 42 having a proximal end 44 and a distal end 46. First and second electrodes 48 and 50 are disposed near the distal end 46 of shaft 42, while a handle 42 is disposed at the proximal end 44 of shaft 42. A switch 44 can be incorporated to apply an RF electrical potential across the first and second electrodes 48, 50. According to one feature, the relatively low RF power level required to heat the electrically conductive structure in sling 206 also inhibits or prevents the tissue from being heated directly, thus eliminating injury to the tissue. Due to the low power requirements, the RF probe can be battery-operated.

As shown in FIG. 4B, the temperature of probe 40 can be measured in situ with a thermal sensor 62, such as a thermocouple or thermistor, and read out by temperature controller 60. The temperature controller 60 can also be used to control the RF power to prevent excessive heating of the distal end 46 proximate to the tissue, or to control the temperature of a coolant which can optionally be supplied to the probe end 46.

Alternatively, the temperature of the sling material can be measured, for example, with an embedded electric probe, such as a thermocouple or thermistor, or an optical probe. Alternatively, the temperature-dependent properties of the conductive material itself, such as the aforedescribed Panion™ polymer material, may be used for temperature measurements. According to one illustrative embodiment, to promote collagen shrinking and prevent irreversible cell damage (necrosis), heating of the surrounding tissue is limited to temperatures between about 60° C. and about 90° C., and in one implementation to between about 60° C. and 80° C.

As mentioned before, a probe 40 with a single electrode, such as electrode 48, may be used for supplying RF energy. As mentioned above, the counter-electrode may be implemented as a large-area ground plate attached external to the patient's body.

For inductively coupling the RF energy, for example, to the loop depicted in FIG. 2E, the two electrodes 48 and 50 of FIG. 4A are replaced by an RF coil (not shown) which can be energized by the RF generator 58 as described above. The magnetic field produced by the RF coil induces an electric current in the conductive loop disposed on or in the sling 206. As mentioned above, the distal end 46 of the probe 40 with the RF coil need not be in physical contact with the sling 206 to induce the current in the loop and heat up the sling 206 and the surrounding tissue. Inductive coupling between RF probe 40 and sling 206, unlike capacitive coupling, does not directly heat the tissue.

To aid spreading of the generated heat across the sling or portions of the sling, the material of the sling may also be thermally conductive. The thermal conductivity of the sling material may be enhanced by embedding in the sling materials that are capable of increasing the thermal conductivity of the sling. Such materials could be metals and/or ceramics and are preferably biocompatible.

Figure 6:
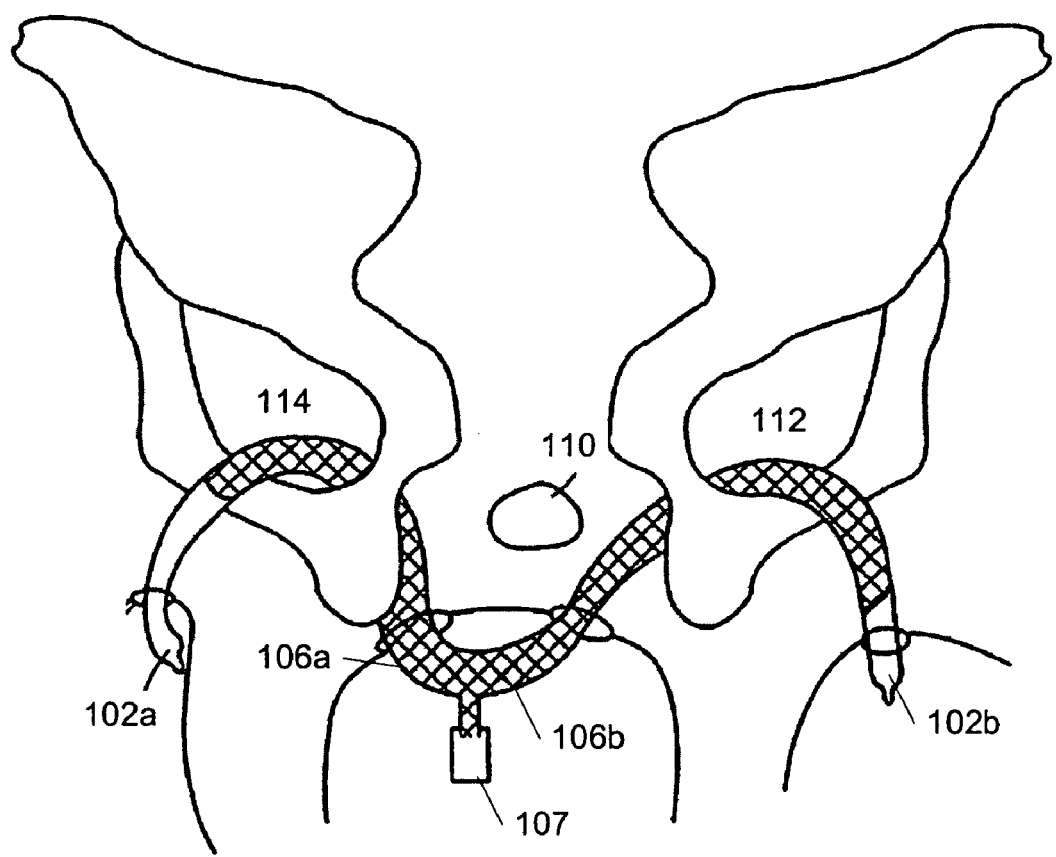
FIG. 6 is a conceptual diagram showing a supportive sling with a center tab and end terminations for attachment to an obturator membrane.

In another illustrative embodiment depicted in FIG. 6, an exemplary electrically or thermally conductive sling assembly 106 is configured to have a centering tab 107 that receives energy from an external source and conducts the energy to the sling 106. More particularly, the centering tab 107 of FIG. 6 divides the sling assembly 106 into two thermally and/or electrically conductive sections, 106a and 106b, having first 102a and second 102b end terminations that are inserted through the obturator foramen 804 and 802 (i.e., transobturally), respectively. The centering tab 107 of FIG. 6 is electrically and/or thermally conductive and is configured to receive energy from a source, such as probe 40, provided through the transvaginal incision. In an exemplary implementation, the centering tab 107 is electrically conductive and configured to attach to an electrode for receiving electrical energy. Alternatively or in addition, the tab 107 may be thermally conductive and configured to receive externally generated heat by clamping or otherwise attaching to a heated tool.

The energized centering tab 107 of FIG. 6 electrically and/or thermally conducts the energy out through the conductive sling material of sections 106a and 106b, raising the temperature of the sling 106 and the surrounding tissue to stimulate tissue growth for supporting the sling 106. In an exemplary implementation, the energy provided to the sling 106 raises the temperature of the tissue surrounding the sling 106 to a temperature of greater than about 37° C., or even greater than about 45° C. In certain implementations, the surrounding tissue rises to a temperature of between about 45° C. and about 50° C.

In another exemplary configuration, the temperature of the sling 106 and surrounding tissue is raised via the delivery devices that are used to insert the end terminations 102a and 102b through the obturator foramen 114 and 112. More particularly, such delivery devices may be configured to deliver electric or thermal energy directly to the sling 106 when inserting the end terminations 102a and 102b into the foramen 804 and 802.

While the invention has been disclosed in connection with the illustrative embodiments shown and described in detail, various modifications and improvements may be made thereto without departing from the spirit and scope of the invention. By way of example, although the illustrative embodiments have been described in conjunction with a supportive sling for treating urinary incontinence, other applications can be contemplated. For example, the electrically energized support structure of the invention may be used to treat male incontinence, hernias, and other ailments where muscle tissue which has slackened for a variety of reasons needs to be strengthened or tightened. Accordingly, the spirit and scope of the invention is to be limited only by the following claims.

What is claimed is:

1. A sling assembly for supporting an anatomical location in a patient comprising:
   an implantable sling sized and shaped for providing support to tissue at the anatomical location, said sling configured for implantation in the periurethral tissue of the patient, and
   an electrically conductive element disposed in or on the implantable sling and couplable to an electromagnetic excitation source, wherein the electrically conductive element produces thermal energy.

2. The sling assembly of claim 1, the sling further comprising end terminations, wherein the electrically conductive element extends between the end terminations of the sling.

3. The sling assembly of claim 2, wherein said electrically conductive element comprises low-resistance end portions located proximate to the end terminations, and one or more additional portions electrically connected either directly or indirectly to the low-resistance end portions, said additional portions having an electrical resistance greater than that of the end portions.

4. The sling assembly of claim 3, wherein the additional portions having the greater electrical resistance are made of a different material than the end portions.

5. The sling assembly of claim 3, wherein the additional portions having the greater electrical resistance have a reduced thickness compared to the end portions.

6. The sling assembly of claim 3, wherein the additional portions having the greater electrical resistance comprise a perforated conductive sheet.

7. The sling assembly of claim 2, further comprising contact portions disposed on or near the end terminations for connection to an external source of electric energy.

8. The sling assembly of claim 2, further comprising contact portions disposed on or near the end terminations for connection to an internal source of electric energy implanted in the body of a patient.

9. The sling assembly of claim 1, wherein the electrically conductive element extends over a portion of the sling.

10. The sling assembly of claim 9, wherein the portion of the sling is the portion intended for supporting the tissue at the anatomical location.

11. The sling assembly of claim 9, wherein the electrically conductive element comprises at least one electrically conductive strand.

12. The sling assembly of claim 11, wherein the electrically conductive strand is woven into the sling.

13. The sling assembly of claim 11, wherein the electrically conductive strand is applied to the sling.

14. The sling assembly of claim 11, wherein the electrically conductive strand is selected from the group consisting of metal wire, metal-coated plastic, metal-coated insulator, metal-dispersed insulator, semiconductor, and conductive polymer.

15. The sling assembly of claim 11, wherein the electrically conductive strand comprises a plurality of strands that are substantially non-overlapping.

16. The sling assembly of claim 11, wherein the electrically conductive strand comprises a plurality of strands that are overlapping at predetermined contact points so as to form electrically conducting loops.

17. The sling assembly of claim 1, wherein the electrically conductive element comprises a dispersed electrically conducting material.

18. The sling assembly of claim 1, wherein the electrically conductive element heats up in response to energy supplied by the electromagnetic excitation source.

19. A system for applying thermal energy to an anatomical location in a patient comprising:
   an implantable sling sized and shaped for providing support to tissue at the anatomical location, said sling configured for implantation in the periurethral tissue of the patient,
   an electrically conductive element disposed in or on the sling, and
   an electromagnetic excitation source coupling energy to the electrically conductive element for conversion into thermal energy.

20. The system of claim 19, wherein the electromagnetic excitation source produces a radio-frequency (RF) field.

21. The system of claim 20, wherein the RF field is resistively coupled to the electrically conductive element.

22. The system of claim 20, wherein the RF field is capacitively coupled to the electrically conductive element.

23. The system of claim 20, wherein the RF field is inductively coupled to the electrically conductive element.

24. A method for supporting an anatomical location in a patient, comprising:
   implanting a sling sized and shaped for providing support to tissue at the anatomical location, said sling configured for implantation in the periurethral tissue of the patient,
   coupling an electromagnetic excitation source to an electrically conductive element disposed in or on the sling to produce thermal energy, and
   heating the tissue proximate to the anatomical location by applying to the tissue the thermal energy produced by the electrically conductive element.

25. Use of a supportive sling having an electrically conductive element disposed in or on the sling for treatment of urinary incontinence, comprising:
   implanting the sling in the periurethral tissue of a patient,
   coupling an electromagnetic excitation source to the electrically conductive element to produce thermal energy, thereby heating the tissue proximate to the anatomical location and strengthening or tightening the tissue to provide added support for the urethra.

26. A method for removing an implanted sling from an anatomical location in a patient, comprising:
   coupling an electromagnetic excitation source to an electrically conductive element disposed in or on the sling to produce thermal energy, thereby heating the tissue proximate to the anatomical location, and
   applying a pulling force to the sling to pull the sling away from the anatomical location.

27. A sling assembly for supporting an anatomical location in a patient comprising:
   an implantable sling sized and shaped for providing support to tissue at the anatomical location, said sling configured for implantation in the periurethral tissue of the patient, and
   heat-conductive element disposed in or on the implantable sling and couplable to a heat source.

* * * * *